United States Patent [19]
Weissman

[11] Patent Number: 5,205,744
[45] Date of Patent: * Apr. 27, 1993

[54] DUAL POSITION SELF POWERED DENTAL DEVICE

[76] Inventor: Bernard Weissman, 225 E. 48th St., New York, N.Y. 10017

[*] Notice: The portion of the term of this patent subsequent to Aug. 20, 2008 has been disclaimed.

[21] Appl. No.: 616,114

[22] Filed: Nov. 20, 1990

Related U.S. Application Data

[63] Continuation-in-part of Ser. No. 353,999, May 19, 1989, Pat. No. 5,040,977, which is a continuation-in-part of Ser. No. 179,332, Apr. 8, 1988, Pat. No. 4,954,082.

[51] Int. Cl.⁵ .............................................. A61C 1/07
[52] U.S. Cl. ..................................... 433/122; 433/125
[58] Field of Search ............... 433/122, 123, 124, 125, 433/131, 133

[56] References Cited

U.S. PATENT DOCUMENTS

| | | | |
|---|---|---|---|
| 491,499 | 2/1893 | Sharp | 433/128 |
| 656,124 | 8/1900 | Kinnison | 433/124 |
| 3,552,022 | 1/1971 | Axelsson | 433/122 |
| 3,939,599 | 2/1976 | Henry et al. | 433/131 |
| 4,276,025 | 6/1981 | Straihammer | 433/133 |
| 4,315,741 | 2/1982 | Reichl | 433/125 |
| 4,781,589 | 11/1988 | Bareth | 433/122 |

*Primary Examiner*—John J. Wilson
*Attorney, Agent, or Firm*—Barry G. Magidoff; Paul J. Sutton

[57] ABSTRACT

This invention provides a self-powered dental hygiene device having an outer housing with three sections, a battery section at one end, an intermediate electric motor section and at the second end a transmission section with a head end section at the distal end. The head end section includes an aperture extending fully therethrough so as to be open at both ends, transverse to the transmission section and designed to hold from either end a replaceable dental bit designed for reciprocating longitudinal motion. The casing is shaped such that the first battery section extends at an angle of between 7 and 12 degrees relative to the transmission section, and the aperture is preferably perpendicular to the axis of the transmission section. The dental tool bit held within either end of the aperture has a hollow plenum for containing a fluid to be administered during use and a pressurizing means is secured to the tool to provide for the expression of the fluid through openings in the tool blade. There is also provided means to resiliently restrain the dental tool bit from rotating relative to the tool.

10 Claims, 8 Drawing Sheets

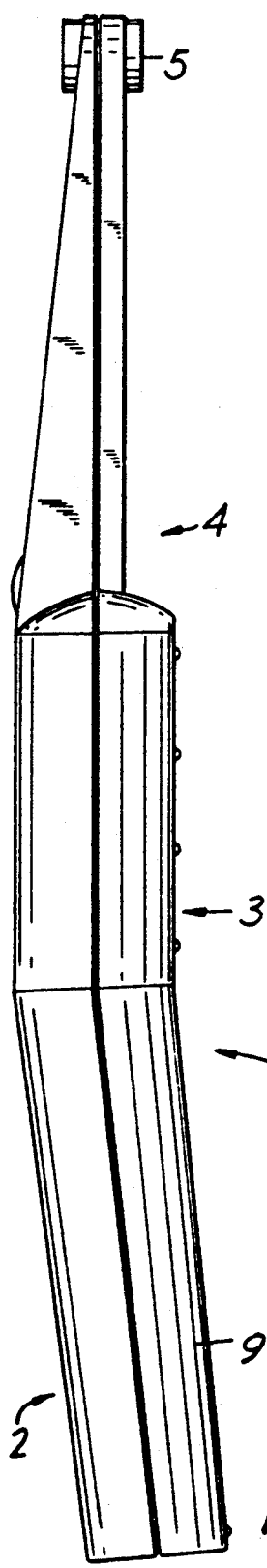
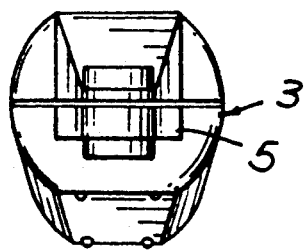
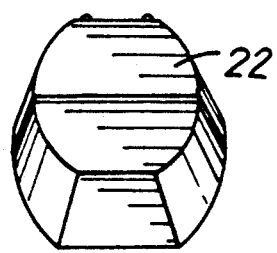
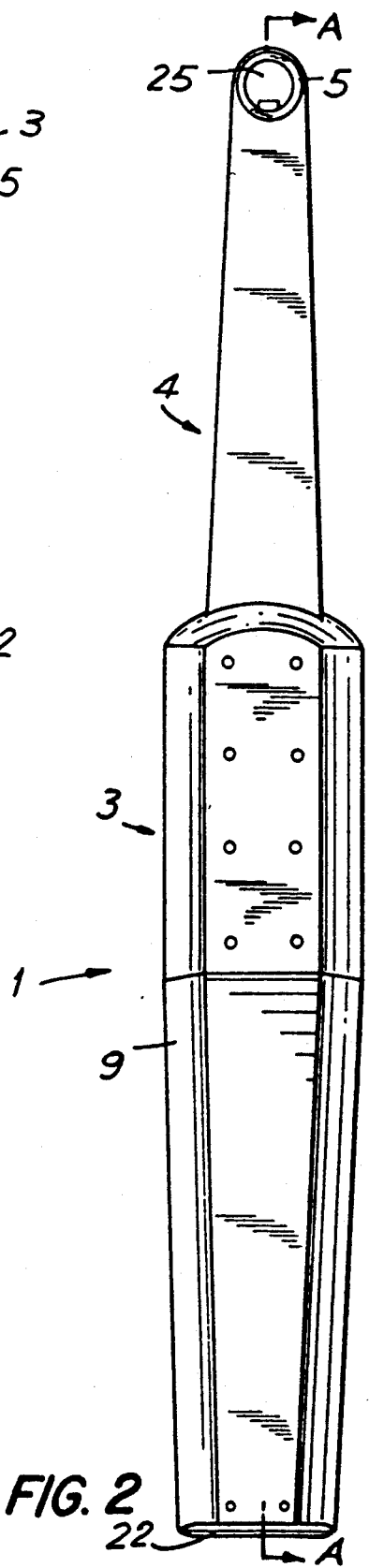
FIG. 5a
FIG. 5b
FIG. 3
FIG. 2

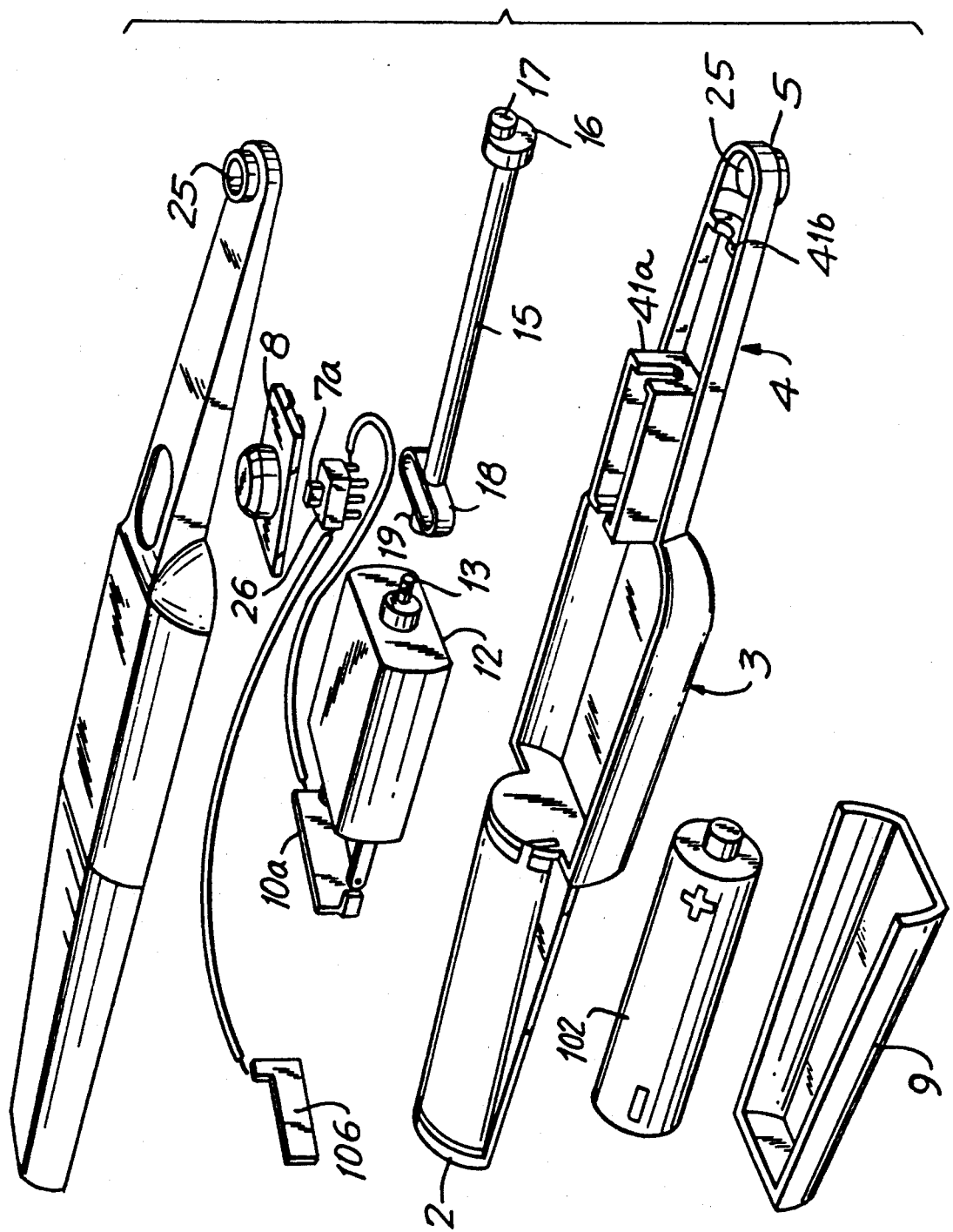

DUAL POSITION SELF POWERED DENTAL DEVICE

BACKGROUND OF THE INVENTION

This is a continuation-in-part of application Ser. No. 353,999 filed on May 19, 1989, now U.S. Pat. No. 5,040,977, which is a continuation-in-part of application Ser. No. 179,332, filed on Apr. 8, 1988 now U.S. Pat. No. 4,954,082.

The present invention relates to a hand-held, internally or self-powered, reciprocating plaque-preventing tool which permits safe use by the general consumer for personal dental hygiene. A removable plaque preventing tool bit is provided, preferably with means to pre-set the angular relationship between the tool bit and the handle, and can further be provided with internal means for simultaneously applying a fluid medium, such as dental cleaning paste, to teeth while reciprocating the bit, for cleaning or polishing the teeth.

There has previously been successfully provided a mechanically driven hand piece, which can be readily powered by a conventional rotary dental drill, to provide reciprocating motion of the type preferably used when abrading or filing teeth or removing excess restorative material, such as hardened dental amalgams or dental composite materials. Such abrasive methods, depending upon the hardness of the abrasive material and the rapidity and pressure with which the abrading surface is applied, can be used to either remove hardened amalgam or dental enamel or to merely remove plaque and to clean and polish teeth surfaces, including both the major lingual and facial surfaces of teeth as well as the interproximal surfaces bordering the teeth interspaces.

A reciprocating handpiece which has been used, by dentists, powered by the dentist's office drill, e.g., is the device described in U.S. Pat. No. 3,552,022 to Axelsson, and commercially available as a Dentatus EVA Reciprocating Motor-Driven Handpiece; this has been used for both purposes, blades with or without embedded abrasives.

It is also known to utilize a syringe type of device to apply toothpaste and the like material for dental hygienic cleaning prior to application of either a mechanically driven or manually operated tooth cleaning means, whether for clinical use or for home use. Such a device is shown, for example, in U.S. Pat. No. 4,411,623 to Axelsson.

SUMMARY OF THE INVENTION

It is an object of the present invention to provide a safe means for individuals to remove, by a reciprocating wiping tool, bacterial colonies and the nutrients film which can result in dental plaque formation, if not dislodged. It is a further object to provide means which render easily accessible the entire mouth surface to a suitable dental tool. It is still a further object to assist such mechanical removal by providing means for simultaneously applying a cleaning fluid, or other therapeutic prophylactic medium, to the teeth while mechanically dislodging debris or polishing the teeth using a portable, self-powered, or battery operated, tool and to provide safe mechanical stimulation to the gums. It is a further object of the present invention to continuously administer such fluid medium through a disposable mechanically driven tool bit which can be hygienically filled and refilled during a single continuing procedure. It is a further object to provide a tool bit (for use with a powered handle) of a size, shape and material which can be molded of plastic sufficiently economically for one-time use, thus further reducing any risk of contagious infection.

It is also an object of the present invention to restrain relative rotation of the cleaning and stimulating tool bit under normal cleaning force, so as to permit accurate positioning and manipulation of the tool, while preventing injury from the accidental application of excessive force.

The self-powered dental hygiene device of the present invention comprises an outer housing having three sections: a first end section designed to hold an electric battery, a first intermediate section containing a rotary electric motor, a second intermediate section containing mechanical transmission means, and a second end head section, adjacent the transmission means and distal the electric motor, comprising means for holding a replaceable film-removing wiping tool bit. Preferably the head section provides dual position tool holding means, for holding the tool bit in either of two opposing positions, to simplify reaching substantially any portion of the mouth. Electrical conducting means are provided between the battery section and the electric motor. The transmission means converts the rotary motion of the electric motor to reciprocating motion. Switch means are provided movably secured to the housing for completing and breaking an electric circuit between the battery section and the electric motor.

The replaceable tool bits can be hollow and secured to fluid pressure means on the housing for causing the flow of e.g., a cleaning fluid into and through the tool bit.

Limited restraining means for the tool bit can be provided in another preferred embodiment of this invention, most preferably in both positions of the dual position head, for presetting the angular relationship between the housing and the tool bit blade and for restraining rotation of the tool bit during operation, while providing for rotation of the bit upon the application of a greater than maximum permitted force; at such greater force, the restraint breaks away and the tool blade is permitted to rotate to avoid injury to the user. Such angular restraint is provided by interaction between the tool bit and holding means secured to the housing.

BRIEF DESCRIPTION OF THE DRAWINGS:

Preferred embodiments of this invention are further described below, by way of example and not exclusion, by reference to the accompanying drawings which display certain portions of the present invention in schematic form. The details of such schematically shown portions will be readily known to those skilled in the art based upon the following verbal descriptions. Referring to the drawings:

FIG. 2 is a bottom view of the tool of FIG. 1;

FIG. 3 is a side view of the tool of FIG. 1;

FIG. 5a is a head view of the tool of FIG. 1;

FIG. 5b is a base view of the tool of FIG. 1;

FIG. 7 is an exploded isometric view of the tool of FIG. 1;

DETAILED DESCRIPTION OF PREFERRED EMBODIMENTS

Figure 1:
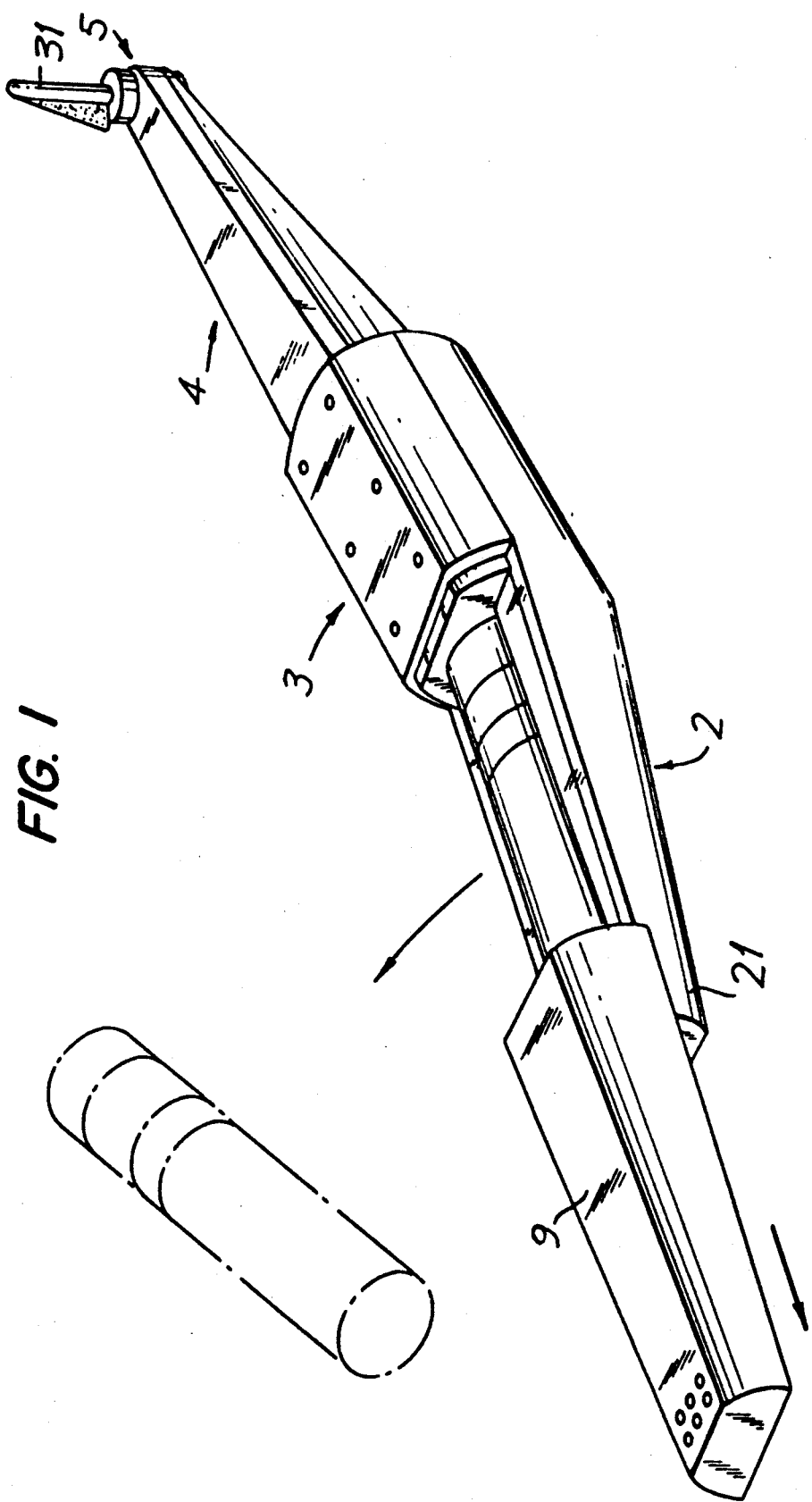
FIG. 1 is an isometric view of a self-powered dental hygiene device of this invention.
Figure 6:
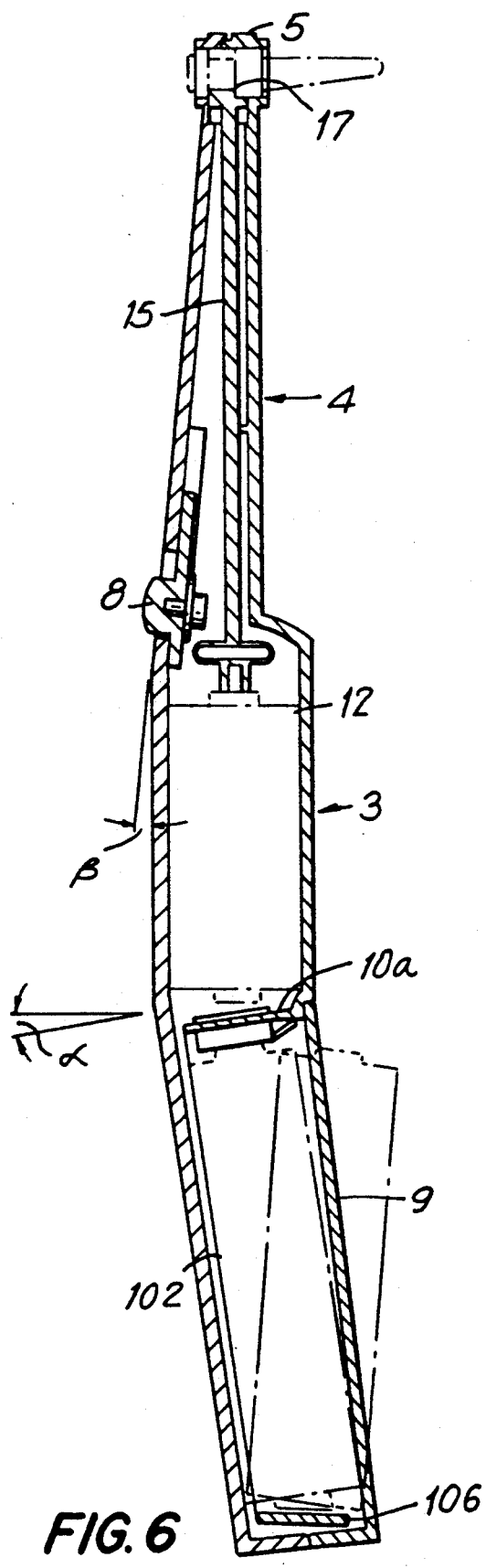
FIG. 6 is a cross-section view taken along lines A—A of FIG. 2.
Figure 4:
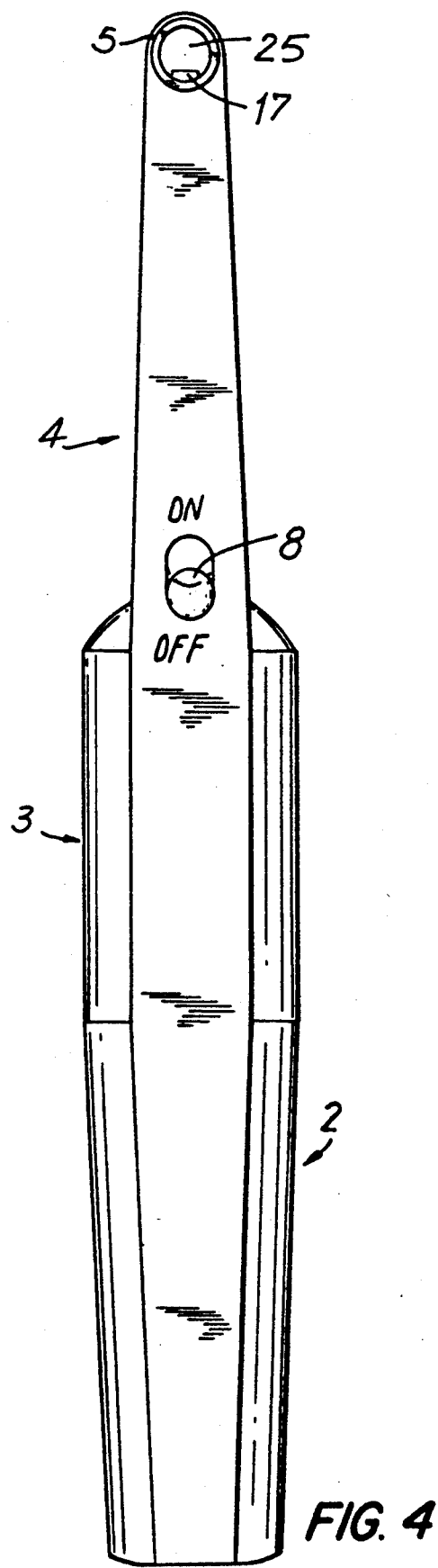
FIG. 4 is a top view of the tool of FIG. 1.
Figure 8:
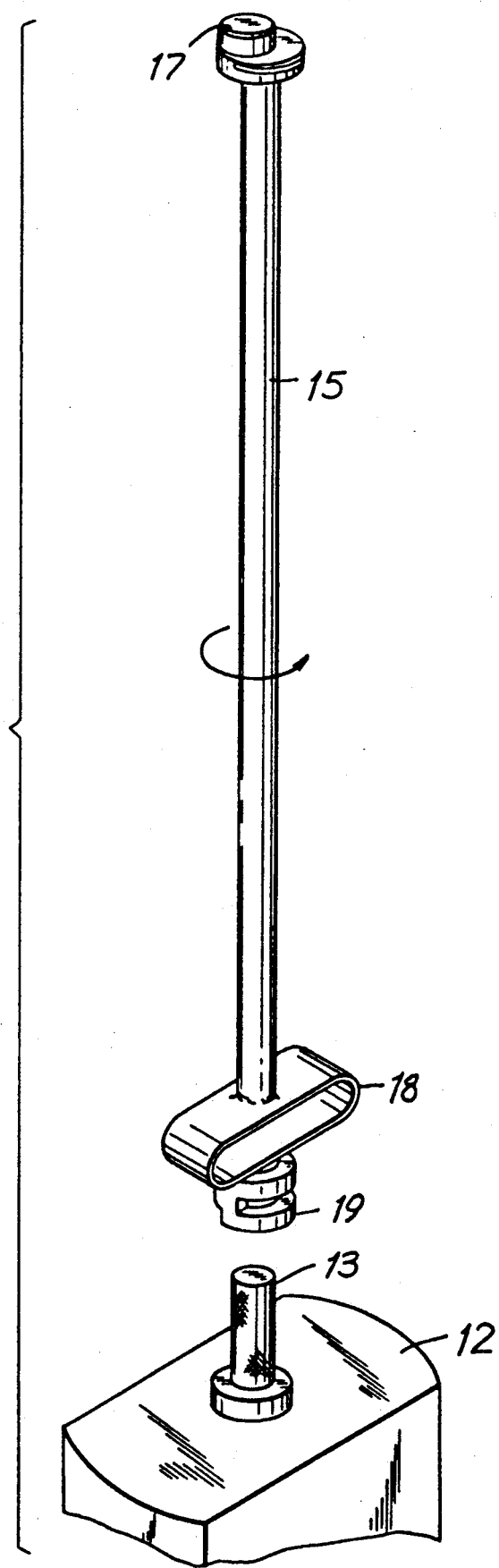
FIG. 8 is an enlarged exploded isometric view of the transmission system of the tool of FIG. 1.

The hand held device of the present invention is shown in preferred embodiments in the accompanying drawings. Referring to the drawings, the outer housing, generally indicated by the numeral 1, is formed into a shape which is easily held and manipulated by a single adult human hand, and is thus suitable for single handed use. The housing comprises a wider, lower portion which forms the battery end section, generally indicated by the numeral 2, which is adjacent an electric motor central portion, generally indicated by the numeral 3, which is adjacent at its top end to a transmission section, generally indicated by the numeral 4, and a tool bit head 5, and which is formed as a preferably molded plastic unit.

The battery section end portion 2, includes a slidably removable cover 9, which can be removed to expose the interior of the battery section for replacement of commercially available, e.g., dry-cell, batteries. Alternatively, permanently affixed rechargeable batteries can be utilized with a recharging socket located at the bottom end 22. When the battery is permanently in place, the slidable cover section 9 need not be used and a permanently affixed portion provided.

Immediately adjacent the battery section 2 is the electric motor section 3, centrally located on the case, and in turn immediately adjacent the transmission section 4. The motor section 3 houses an electric motor 12, which is in electric circuit connection with a battery 102 in the battery section 2, and is mechanically linked to a transmission shaft 15 within the transmission section 4. The electric motor 12 is in switchable electric circuit connection to the battery terminals 10a, 10b, the circuit being closable by an on/off switch button slide 8, located in the case 1 at the boundary between the motor section 3 and transmission section 4.

In this preferred embodiment, the switch slide 8 includes a surface in contact with a spring loaded circuit connector 7a, located within the case 1, and thus when the button 8 slides towards the head 5 of the device, it presses inwardly on the spring loaded circuit connector 7a, in circuit switch 7b, to close the circuit and to permit electricity to flow from the battery 102 to the electric motor 12. Sliding the switch button 8 towards the battery section 2, releases the spring loaded circuit connector 7a, causing an interruption in the circuit and shutting off the motor 12. Alternatively, the switch can be pressed inwardly and in that position the switch button 7a is held in the closed circuit position, and springs back to the open circuit position when pressure is released. For certain circumstances, it may be preferable to require this type of spring-loaded switch, such that the operation of the motor immediately halts upon the releasing of the switch 8.

A battery is in place within the battery section 2 and releasably held such that the positive terminal of the battery is in direct contact with the circuit terminal 10b and the negative end of the battery is in direct connect with the other circuit terminal 10a. Electrical conductors connect the two terminals 10a, 10b to the electric motor 12 and to the switch 7a, 7b.

A transmission shaft 15 is slidably and rotatably held within the transmission section 4 by interior guide members 41a,b. The outer end of the transmission shaft 15 is secured to a radially extending transverse end portion 16, which includes an eccentrically located cam button 17, at the outer circumference of the transverse member 16.

A knurled driving shaft 13 (or other non-slip connection) extends axially outwardly from the electric motor towards the tool head 5. The driving shaft 13 extends into a centrally formed, mating female portion 19 affixed to the lower end of the transmission shaft 15. The interior surface of the female portion 19 firmly holds the knurled end 13 of the driving shaft so as to limit relative rotational slip between the surfaces.

The transmission shaft 15 further comprises an axially resilient member, such as the compression loop spring 18, preferably located adjacent the female holding member 19. The compression loop spring 18 permits limited resilient axial movement of the transmission shaft 15 within the transmission section 4. Alternatively, a helical spring can be provided between the motor driving shaft 13 and the transmission shaft female portion 19.

The transverse head member 16 and the eccentric cam button 17 extend into the head portion 5 of the tool case. The head portion 5 defines a central opening 25, extending through the tool case 1, in an axial direction transverse to the axis of the drive shaft 15. The eccentric cam button 17 extends into the transverse opening 25.

Rotary motion of the transmission shaft 15 is converted to linear reciprocating motion along a transverse axis, by the action of the eccentric cam button 17 between two annular surfaces on a transmission collar slidably held within the tool head portion 5. The collar can comprise two outer flanges, supporting the annular surfaces, and an intermediate neck portion of a smaller diameter. The eccentric cam button 17 can rotate between the two flanges, preferably out of contact with the neck portion.

Figure 9:
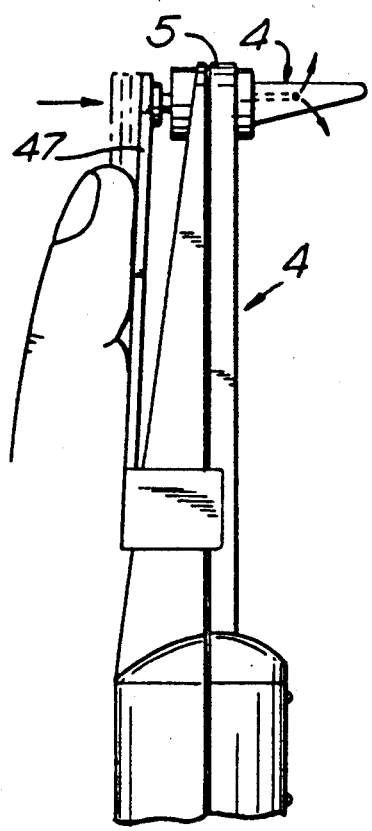
FIG. 9 is a partial side view of a tool with a fluid dispensing bit.
Figure 10A:
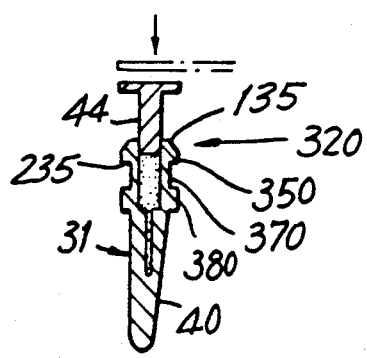
FIG. 10a is a cross-sectioned elevation view of the tool bit of FIGS. 9 and 10.
Figure 10:
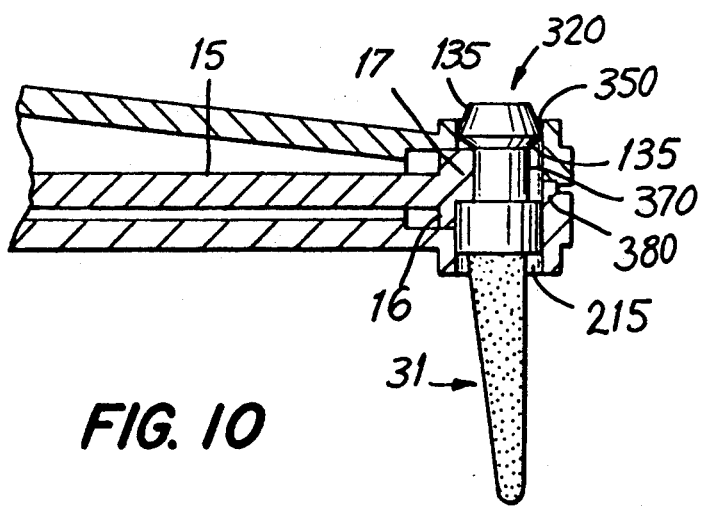
FIG. 10 is a cross-sectioned partial side elevation view of the head portion of the tool of this invention with a fluid dispensing embodiment of a dental tool bit in place.
Figure 12:
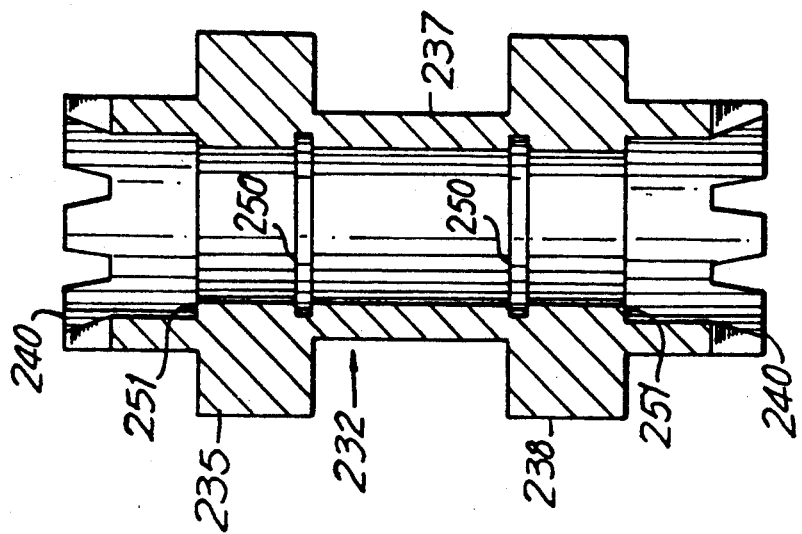
FIG. 12 is a cross-section view of the fixed collar of FIG. 11.
Figure 11:
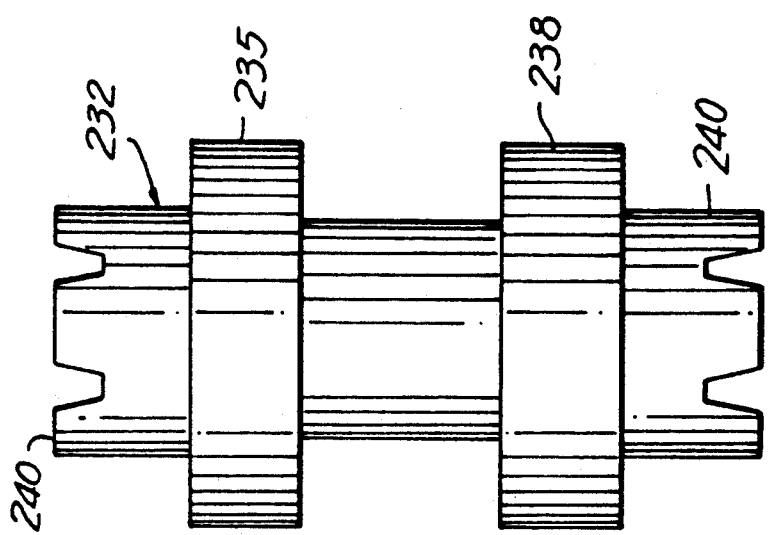
FIG. 11 is an enlarged elevation view of another embodiment of the fixed collar, including a dual position tool holder.
Figure 13:
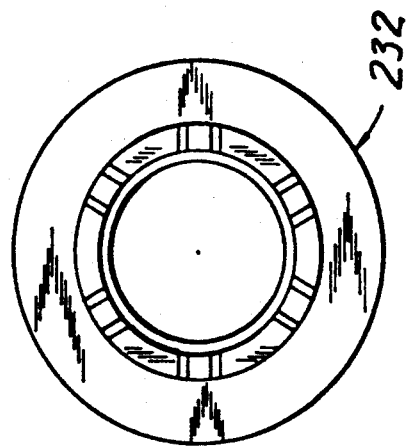
FIG. 13 is an end view of the fixed collar of FIG. 11.
Figure 14:
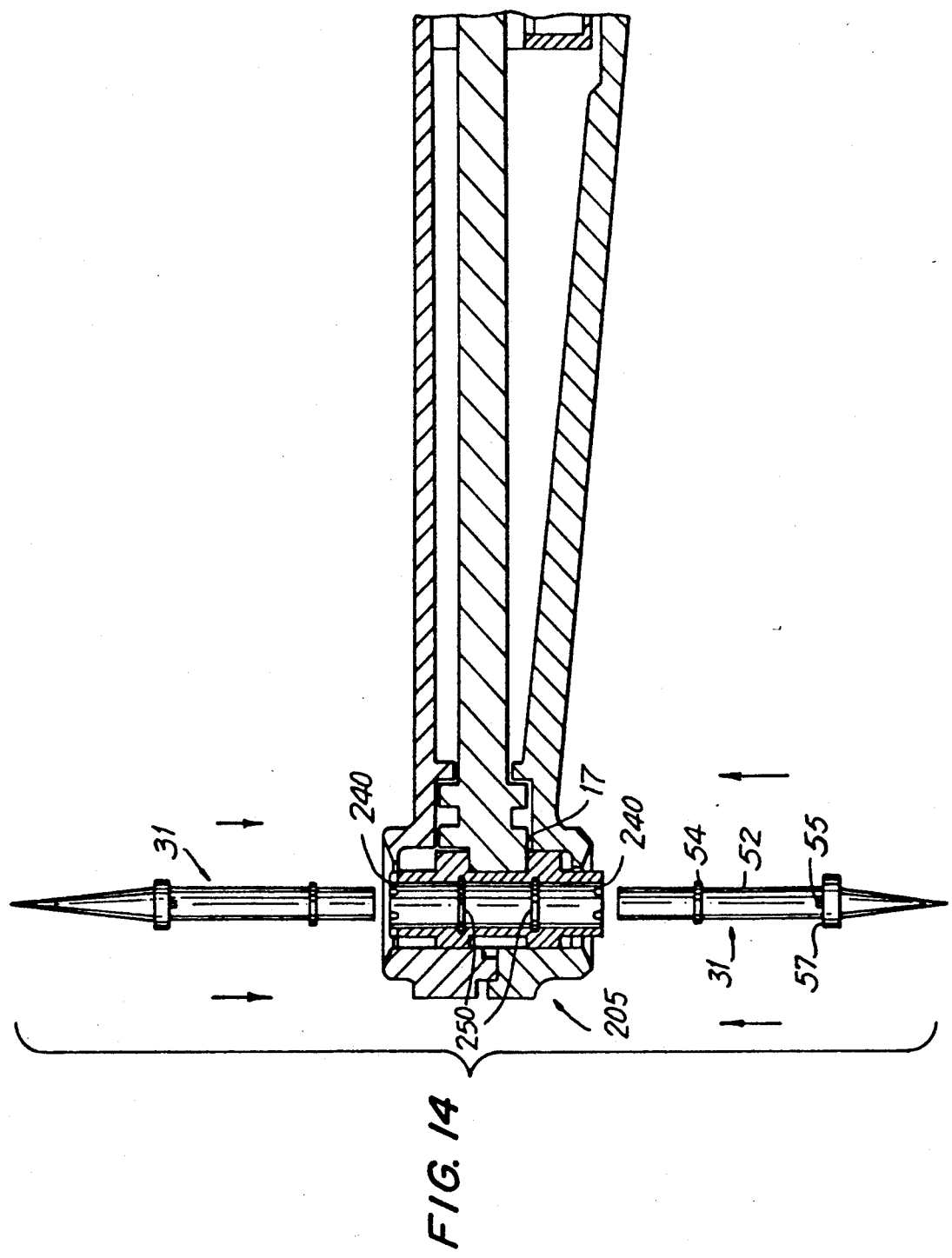
FIG. 14 is a cross-section view of another embodiment of the headpiece of the present invention, including a dual position collar in accordance with FIG. 11.

Referring to the embodiment of FIGS. 9, 10 and 10a, a transmission collar, generally indicated by the numeral 320, is formed integral with the tool bit 31. The collar 320 comprises a beveled outer flange 350 and an inner flange 380 surrounding a collar shank 370. The eccentric cam button 17 extends between the two flanges 350, 380.

Dental tool bits, for example, the paste-dispensing bit 31 shown in the drawings, are designed to be of various shapes and surface textures for dislodging of films of food particles and micro-organisms from various teeth surfaces and are held within the central head aperture 25.

In the embodiment of FIGS. 9 and 10, when the bit is attached, into the head portion 5, the outer flange 350 is pushed first into the bottom opening of the central head aperture 25. The beveled outer end 135 of the outer flange 350 pushes against the eccentric cam button 17 causing the transmission shaft 15 to move axially towards the electric motor 12, compressing the spring loop 18 until the outer flange 350 moves beyond the button 17 and the button springs back and is supported adjacent the collar shank 370, between the two flanges 350, 380. When the tool bit 31 is removed, the inner bevel 235 pushes aside the cam button 17. The bit 31 is thus releasably retained within the aperture 25 by the eccentric cam button 17.

In another embodiment a permanent collar, is secured in to the head portion aperture 25, so as to be reciprocally movable. The collar comprises an outer flange and an inner flange, with a shank (of lesser diameter) therebetween. The eccentric cam button 17 extends towards the collar shank between the two flanges. A central opening through the permanent collar 32 can receive a second embodiment of a tool bit. Extending from the inner flange is a notched sleeve, the notches opening outwardly, the sleeve defining the end of the central opening. The collar can be restrained from rotating by a detent means interacting with a mating portion on the interior surface of the head aperture 25, e.g. a wedged sphere in the interior surface and an axially extending notch on the outer surface of the flanges or by forming the interior cross-section of the head aperture 25 and exterior cross-section of the collar to be mating polygons, or to be other than circular. It is noted that in this embodiment there is not need for a compression spring in the transmission shaft 15, as the shaft 15 need not be axially movable. In a combination situation, a semi-fixed collar can be removably juxtaposed with a resiliently movable shaft 15 to enable alternative use of the two types of tool bits.

The tool bit in this embodiment can be formed, e.g., of a hard, but flexible, thin molded plastic, such as polycarbonate. The blade portion has opposing major surfaces which can be triangular in plan, tapering to a rounded bottom apex. One edge of the blade is preferably thinner, to cause insertion between teeth. The major surfaces can be textured, or coated with fine abrasive particles.

The shank of this bit is substantially cylindrical from the top of the blade to the end. A slightly enlarged, annular rib 54 is formed adjacent the top end to mate with the annular notch, formed on the interior of the fixed collar 32. The blade shank 52 is split through its upper portion by a slit so that the shank can be compressed while being inserted into the fixed collar 32, and will then snap back so that the rib 54 locks into the notch to axially secure the bit relative to the collar 32.

A resilient spur 55 is formed at the top of the blade and mates with any of the a notches 140 to pre-set the angular relationship between the bit blade and the hand piece transmission shaft axis, "X".

In the most preferred embodiments, the tool bit 31, is capable of being pre-filled with a unit dosage amount of a fluid material, such as tooth paste, or the like cleansing fluid. In this embodiment, a plunger 44, for example, can be provided, which when pressed will force any fluid held within a plenum chamber 45, within the bit to be discharged through thin pores formed through the wall of the blade 40. The plunder 44 can be pressed directly by the operator's finger or by a resilient arm, secured to the outer housing of the transmission portion 4 (as shown in FIG. 9); such a resilient arm 47 can provide desirable helpful leverage especially for users with small hands, or short fingers. Such a plunger 44 can be provided with any embodiment of the tool bit, i.e., with an integral collar (bit 31) or for use with a fixed collar.

The ability to either preset the relative angle between the blade and the handle enables the user to comfortably hold the handpiece regardless of the location in the mouth to be cleaned. When a slightly greater versatility is required and when the effort required to dislodge, e.g., a piece of hard food caught in the teeth, is not needed, the bit can be permitted to freely rotate by not engaging the rotation resisting members (e.g., the spur 55 and notches 240).

The tool housing 1, described herein and as shown in the drawings, is designed to be easily held in a single hand of the user; thus, the widest point of the battery portion 2 of the housing, which comprises the principal handle, should be sufficiently narrow to be easily held during use. The transmission section 4 is preferably angled with respect to the battery section 2, and extends a sufficient distance from the motor section 3 to permit applying a dental tool bit 31 supported from the head aperture 25 to reach even the rear molars of the user. Thus, the transmission section 4 is preferably from about 4 ins. to about 6 ins. in length to accommodate the longest dental arch. The transmission section 4 and the electric motor section 3 are substantially coaxial. Preferably, the angle ($\alpha$) between the axis of the motor section 3 and transmission section 4 and the axis of the battery section 2 is preferably at least about 6', and most preferably in the range of from about 7 to about 12 degrees, to provide the desired ease of reaching any teeth in the mouth. The angle between the top surface of the motor portion 3 and the transmission portion top surface 4 is in the range of from about 4 degrees to about 8 degrees. (Angle B)

The bottom end surface 21, is so juxtaposed with respect to the axis of the battery portion 2, as to permit standing the dental device on its end. The angle of the bottom end surface 21 relative to the axis of the battery section 2 is dependant upon the location of the center gravity of the overall device, when the battery and a tool bit are in place. The center of gravity must be directly above, preferably, a central portion of the base surface 21.

In operation, after a tool bit (31 and 45) has been pressed into position through the head aperture 25, and the cam button 17 is in place between the collar flanges (35, 38 or 350, 380), the switch 8 is slid towards the head 5, starting the electric motor. Rotation of the driving shaft 13 in turn causes rotation of the transmission shaft 15, causing the eccentric cam button 17 to rotate and to move axially with respect to the tool bit shank portion 37, pressing against the opposed flange surfaces. As the eccentric button 17 rotates and moves transversely to the transmission shaft 15, the tool bit 31 is caused to move reciprocatingly axially, thereby creating the desired reciprocating movement for the tool blade 49.

The tool bit blade 49 is preferably formed of a flexible material such as a plastic, and preferably has a textured or abrasive outer surface. Blades for the final polishing of tooth surfaces can be formed of natural material, such as a laminate of soft leather, or synthetic such surface films. The dental tool bits useful with this invention can include any of the devices set forth for example in co-pending application Ser. No. 172,483 filed on Mar. 24, 1988 or application Ser. No. 179,332 filed on Apr. 8, 1988, the description of the bits being incorporated herein by reference. As in the copending applications referred to above, the bit can rotate about its own longitudinal axis relative to the tool head 5, or the bit can be releasably restrained from rotating by the various means described herein and in the above referred to copending applications.

It is further advantageous to provide for the application of therapeutic fluid while operating the tool bit. The tool bit is formed with at least one thin edge which can fit into the interdental spaces. Tool bits capable of providing for the simultaneous application of, e.g., cleansing material such as toothpaste through the walls of the blade from an internal plenum space are also described for example, in the two copending applications referred to above. One example of such a dispensing bit is shown in FIG. 10a, herewith.

A dual position tool holding head is shown in FIGS. 12 through 15. In this embodiment, the tool 31 can extend from the head, generally indicated by the numeral 205, in opposing directions, thus enabling the user to fully exploit the angles alpha and beta of the tool handle to reach all portions of the dental surfaces. A modified fixed collar, generally indicated by the numeral 232, is retained in the headpiece 205, so as to be reciprocally movable, as described above. This collar 232 also comprises a pair of flanges 238, with a shank 237 (of lesser diameter) therebetween. The eccentric cam button 17 extends towards the collar shank 237 between the two flanges 235, 238, as in the above embodiments. In this embodiment, however, there is a notched sleeve 240 extending rom each end of the collar 232, extending outwardly of each of the flanges 235, 238; the notches 240 open outwardly, the sleeves 240 defining the ends of the central opening 235, as in the above embodiment. The dual position collar interacts with the head in the same manner as described above.

In this embodiment of FIGS. 11-14, there are two internal annular grooves 250 formed centrally on the internal cylindrical surface of the collar, to mate with the annular rib 54 on the tool shank 52, in either of the opposing directions the tool can be held. Similarly, the notches 240 formed at both ends of the fixed collar 232, mate with, e.g., the spurt 55, on the tool bit 31, in either direction. As with the above embodiments, the tool bit 31 can be retained in the collar in two conditions (for each direction): first, when the rib 54 mates into the groove 250, the tool 31 is free to rotate about its long axis; second, when the tool 31 is pushed beyond the groove, so that the end of the tool shaft 57 abuts against an internal shoulder 251, and the spurt 55 mates into one of the notches 240, preventing rotation of the tool.

In a preferred embodiment of the battery provided for the energizing of the electric motor is a conventional AA dry cell battery (1.5 volts output). It has been found that a power output not exceeding about 4 volts, e.g., the power output provided by two such AA batteries, is sufficient to power a tool bit for cleaning the teeth, but is not sufficient to cause injury to the teeth or gum tissue. A tool bit jammed between two teeth can halt the rotary motion of the electric motor before causing injury to the user, either to the gums or to the teeth. A rechargeable battery of about the same voltage can, of course, also be used.

The dental tool of this invention is useful for the cleaning of any mammalian teeth, finding valuable use in veterinary medicine, as well.

It is also useful in a more powerful version, by increasing battery voltage or by connection to an external electrical source, for hobbyists use, as for smoothing wood or plastic, or even metal.

The patentable embodiments which are claimed are as follows:

1. A self-powered hand-held dental device for the cleaning of teeth, the dental device comprising an outer housing; a portion of the outer housing providing a hand grip for the device; within the housing there being provided a battery section, a motor section, a transmission section and a tool bit hear section having a first side and a second side and defining a transverse aperture extending fully there between so as to be open at both ends; the battery section comprising a positive and a negative terminal so juxtaposed as to retain a battery within the housing; an electric motor provided with a driving member within the motor section of the housing; switchable electric circuit means connecting the electric motor with the terminals and a switching means exposed to the exterior of the housing and so juxtaposed with the electrical circuit means as to cause the opening and closing of a circuit gap upon operation of the switch so as to initiate and terminate operation of the electric motor when an electric battery is provided between the terminals; the tool bit head section being located at the end of the transmission section distal the electric motor section; a rotatable transmission shaft held rotatably in the transmission section, one end of which is mechanical operating connection with the electric motor driving member, the distal end of the transmission shaft comprising an eccentric cam member located radially outwardly of the axis of rotation of the transmission shaft and extending longitudinally out of the transmission shaft and extending radially from the axis of the transmission shaft, the eccentric cam member extending into the head section aperture, the aperture extending into the head section along an axis transverse to the axes of the transmission shaft and of the cam; a tool bit, comprising tool head and tool blade, in operating relationship to the eccentric cam member, such that rotation of the transmission shaft causes reciprocating movement of the tool bit transversely of the shaft axis; the tool head having a blade end secured to the blade and a distal end, located with the transverse aperture; the tool head being removably retained within the head section aperture, the head section and the tool head being each so configured that the distal end of the tool head can be inserted into the transverse aperture from either the first side or the second side; a collar axially slidably secured to the tool head with the transverse aperture, the collar comprising a narrow central shank neck and an annular flange at each end of the shank neck, the eccentric cam member facing the shank neck between the two flanges, the collar having an internal circumferential surface defining a central aperture extending completely through the collar so as to be open at each end and capable of holding the head of a tool bit, in the operating relationship of the tool, from each end; cooperating locking means formed adjacent each end of the internal circumferential surface to interact with cooperating means on the tool to prevent axial motion of a tool relative to the collar, and second cooperating locking means formed adjacent each end of the collar to restrict rotation of the tool relative to the collar.

2. The dental tool of claim 1 wherein the dental bit comprises a hollow plenum within a blade portion and pores through the wall of the blade portion to permit passage of fluid held within the plenum out to the outside surface of the blade.

3. The dental device of claim 2 comprising a conduit means extending from the head end of the bit into the bit plenum to provide means for filling the bit plenum with fluid material and to provide means for applying compressive pressure to force the fluid out through the pores.

4. The dental device of claim 1 wherein the transmission section and shaft extend at an angle of from about 7° to about 12° with respect to the axis of the handle portion and wherein the head aperture extends substantially perpendicularly to the axis of the transmission shaft.

5. The dental device of claim 1, comprising spring compression means between the eccentric cam and the motor driving member, to permit resilient axial movement of the transmission shaft when pressure is exerted against the cam having a component in a direction substantially parallel to the transmission shaft axis.

6. The dental device of claim 1, being powered by two AA dry cell batteries.

7. A self-powered hand-held dental device for the cleaning of teeth, the dental device comprising a substantially integral outer housing; a portion of the outer housing providing a hand grip for the device; the housing defining, in axial juxtaposition, a battery section, a motor section, a transmission section and a tool bit head section defining a transverse aperture; the battery section containing a positive and a negative terminal so juxtaposed within the housing as to retain a battery within the housing; and electric motor provided with a rotatable driving member within the motor section of the housing; switchable electric circuit means connecting the electric motor with the terminals and a switching means exposed to the exterior of the housing and so juxtaposed with the electrical circuit means as to cause the opening and closing of a circuit gap upon operation of the switch so as to initiate and terminate operation of the electric motor when an electric battery is provided between the terminals; a head section, having a transverse aperture therethrough, at the end of the transmission section distal the electric motor section; a rotatable transmission shaft held rotatably in the transmission section, one end of which is in mechanical operating connection with the electric motor driving member, the distal end of the transmission shaft comprising an eccentric cam member located radially outwardly of the axis of rotation of the transmission shaft and extending longitudinally out of the transmission shaft but set off radially from the axis of the transmission shaft, the eccentric cam member extending into the tool bit head section aperture, the aperture extending wholly through the tool bit head section along an axis transverse to the axes of the transmission shaft and the cam so as to be open at each end; the transmission section and shaft extend at an angle of from about 7 degrees to about 12 degrees, with respect to the axis of the handle portion, and wherein the tool bit head section aperture extends substantially perpendicularly to the axis of the transmission shaft; a collar slidably secured within the tool bit head section aperture, the collar comprising a narrow central shank neck and an annular flange at each end of the shank neck, the eccentric cam member facing the shank neck between the two flanges, the collar being in operating relationship to the eccentric cam member, such that rotation of the transmission shaft causes reciprocating movement of the collar transversely of the shaft axis; the collar defining a central aperture extending completely through the collar so as to be open at each end, and so designed to be capable of holding the head of a tool bit from either end, such that the tool bit can extend out from either end of the collar and move axially with the collar; cooperative locking means formed adjacent each end of the central aperture to interact with cooperating means on the tool bit and prevent axial motion of such a tool bit relative to the collar, and a second cooperating locking means formed adjacent each end of the central aperture to restrict rotation of the tool relative to the collar.

8. The dental device of claim 7, comprising spring compression means between the eccentric cam and the motor driving member, to permit resilient axial movement of the transmission shaft when pressure is exerted against the cam having a component in a direction substantially parallel to the transmission shaft axis.

9. The dental device of claim 8, wherein the angle between the central plane of the top surface of the motor section and the central plane of the top surface of the transmission section is in the range of from about 4° to about 10°.

10. The dental tool of claim 7 further comprising cooperative locking means formed adjacent each end of the transverse aperture to interact with cooperating means on the collar to restrict rotation of the tool relative to the head section.

* * * * *